(12) United States Patent
Takada et al.

(10) Patent No.: US 7,343,277 B2
(45) Date of Patent: Mar. 11, 2008

(54) PARALLEL COMPUTING METHOD FOR TOTAL ENERGY AND ENERGY GRADIENT OF NON EXPERIENCE MOLECULAR-ORBITAL METHOD

(75) Inventors: Toshikazu Takada, Tokyo (JP); Kazuto Nakata, Tokyo (JP); Tadashi Murase, Tokyo (JP); Toshihiro Sakuma, Kawasaki (JP)

(73) Assignees: Japan Science and Technology Agency, Saitama (JP); NEC Corporation, Tokyo (JP)

( * ) Notice: Subject to any disclaimer, the term of this patent is extended or adjusted under 35 U.S.C. 154(b) by 235 days.

(21) Appl. No.: 10/490,703

(22) PCT Filed: Sep. 25, 2002

(86) PCT No.: PCT/JP02/09871

§ 371 (c)(1),
(2), (4) Date: Aug. 17, 2004

(87) PCT Pub. No.: WO03/027873

PCT Pub. Date: Apr. 3, 2003

(65) Prior Publication Data

US 2004/0260529 A1    Dec. 23, 2004

(30) Foreign Application Priority Data

Sep. 25, 2001 (JP) ............................ 2001-292092

(51) Int. Cl.
*G06G 9/44* (2006.01)
(52) U.S. Cl. .................................................. 703/21
(58) Field of Classification Search .................. 703/3, 703/21; 708/495, 501, 523
See application file for complete search history.

(56) References Cited

U.S. PATENT DOCUMENTS 6,026,422 A * 2/2000 Yamada et al. ............. 708/523

(Continued)

FOREIGN PATENT DOCUMENTS

JP    H09-50458 A    2/1997

OTHER PUBLICATIONS

Hashimoto et a., MOE: A Special-Purpose Parallel Computer for High-Speed, Large-Scale Molecular Orbital Calculation, Nov. 13-18, 1999, Supercomputing, ACM/IEEE 1999 conference, pp. 58-58.*

(Continued)

*Primary Examiner*—Paul Rodriguez
*Assistant Examiner*—Eunhee Kim
(74) *Attorney, Agent, or Firm*—Sughrue Mion, PLLC

(57) ABSTRACT

A parallel computing method by using a parallel computer having a plurality of processors is provided, wherein when a 2-electron integration is transformed from an atomic-orbital base (rs|tu) to a molecular-orbital base (ab|cd), indexes r and s of an atomic orbital to be calculated are designated for the plurality of processors and each of the plurality of processors performs processing for all combinations of designated indexes R and S, and indexes t and u of the atomic orbital to be calculated. Subsequently, the grain sizes are equalized, many commodity processors can be connected with high performance, and the cost of a high-speed operation computer reduces. Further, the computer can obtain a large main-memory area, as a whole, through the use of inexpensive local memories.

11 Claims, 6 Drawing Sheets

U.S. PATENT DOCUMENTS 6,631,391 B1* 10/2003 Inabata et al. .............. 708/495
2003/0167159 A1* 9/2003 Goddard et al. .............. 703/12

OTHER PUBLICATIONS

Satoru Shirakawa et al., "The Architecture of a Molecular Orbital Calculation Engine (MOE)", Information Processing Society of Japan Kenkyu Hokoku, May 16, 1996, vol. 96, No. 39, pp. 45-50.

Adrian T. Wong et al., "Parallel Direct Four-Index Transformations", Theoretica Chimica Acta, Jun. 1996, vol. 93, No. 6, pp. 317-331.

Kazuto Nakata et al., "A parallel Algorithm for Generating Two Electron Integrals Over MO Basis Sets", Information Processing Society of Japan Symposium Ronbun, Jan. 22, 2002, vol. 2002, No. 4, pp. 35-42.

Yukio Hirahara et al., Hikeikenteki Bunshi Kidoho Program (AMOSS) no Heiretsuka, Information Processing Society of Japan Kenkyu Hokoku, Mar. 9, 1995, vol. 95, No. 28, pp. 41-48.

Kazuto Nakata et al., Heiretsu CASSCF Program No Kaihatsu, Bunshi Kozo Sogo Toronkai Koen Yoshishu, Sep. 24, 2001, vol. 2001, p. 764.

* cited by examiner

MOLECULAR-ORBITAL BASE 2-ELECTRON INTEGRATION
GENERATION PARALLEL ALGORITHM

SLAVE PROCESS GROUP (1) DATA TRANSFER: MOLECULAR-ORBITAL COEFFICIENT c

→ [CPU#0]    → [CPU#1]    → [CPU#2]

(2) TRANS-
    FORMATION 1

| | |
|---|---|
| DESIGNATE R AND S<br>　do t<br>　　do u<br>　　　CALCULATE $(RS\|tu)$<br>　　　do d<br>STEP 1 →　　　$(RS\|td) = (RS\|td) + c_{ud}(RS\|tu)$<br>　　　end do<br>　　end do<br>　end do<br>　do d<br>　　do t<br>　　　do c<br>STEP 2 →　　　$(RS\|cd) = (RS\|cd) + c_{tc}(RS\|td)$<br>　　　end do<br>　　end do<br>　end do<br>　do c<br>　　do d<br>　　　do B<br>STEP 3 →　　　$(RB\|cd) = (RB\|cd) + c_{sB}(RS\|cd)$<br>　　　end do<br>　　end do<br>　end do | SAME AS LEFT    SAME AS LEFT |

FIG. 1

ENERGY-GRADIENT CALCULATION PARALLEL
ALGORITHM BY Γ INVERSE TRANSFORMATION

```
do r
 do s
  [PARALLELIZATION BY r AND s]
  do a
   do b
    do c
     do u
      do d
       Γ(abcu) ← Γ(abcd)
      end do
     end do
    end do
    do u
     do t
      do c
       Γ(abtu) ← Γ(abcu)
      end do
     end do
    end do
    do t
     do u
      Γ(aStu) ← Γ(abtu)
     end do
    end do
   end do
   do t
    do u
     Γ(RStu) ← Γ(aStu)
    end do
   end do
  end do
    2-ELECTRON INTEGRATION (R*S|tu) IS CALCULATED FOR ALL t AND u, AND MULTIPLED BY Γ
 end do
end do
```

FIG. 4

KNOWN 2-ELECTRON INTEGRATION $4N^5$-TH
POWER TRANSFORMATION ALGORITHM

STEP 1
   do r
     do s
       do t
         do u
           do d
             (rs|td) = (rs|td) + cud × (rs|tu)
           end do
         end do
       end do
     end do
   end do STEP 2
   do d
     do r
       do s
         do t
           do c
             (rs|cd) = (rs|cd) + ctc × (rs|td)
           end do
         end do
       end do
     end do
   end do STEP 3
   do c
     do d
       do r
         do s
           do b
             (rb|cd) = (rb|cd) + csb × (rs|cd)
           end do
         end do
       end do
     end do
   end do

FIG. 5

STEP 4
```
do b
  do c
    do d
      do r
        do a
          (ab|cd) = (ab|cd) + cra × (rb|cd)
        end do
      end do
    end do
  end do
end do
```

FIG. 6

PARALLEL COMPUTING METHOD FOR TOTAL ENERGY AND ENERGY GRADIENT OF NON EXPERIENCE MOLECULAR-ORBITAL METHOD

TECHNICAL FIELD

The present invention relates to a parallel computing method for total energy and energy gradient by using the multi-configuration self-consistent field (MCSCF) method and the configuration interaction (CI) method of non-experience molecular-orbital method.

BACKGROUND ART

Of the non-experience molecular orbital method, the above-described MCSCF method and CI method have been used as typical computing methods that can use electron correlation. According to the MCSCF method, total energy E and the derivative thereof with respect to an atomic-nucleus coordinate, that is, the energy gradient (a force applied on the atomic nucleus) are given as below.

$$E = \sum_{ab}^{MO} \gamma_{ab} h_{ab} + \frac{1}{2} \sum_{abcd}^{MO} \Gamma_{abcd}(ab|cd) \qquad (1)$$

$$\frac{\partial E}{\partial q} = \sum_{ab}^{MO} \gamma_{ab} \frac{\partial h_{ab}}{\partial q} + \frac{1}{2} \sum_{abcd}^{MO} \Gamma_{abcd} \frac{\partial (ab|cd)}{\partial q} \qquad (2)$$

Here, MO indicates a molecular orbital and q indicates any of the nuclei x, y, and z of an atom forming a molecule. $\gamma$ and $\Gamma$ indicate functions of a coefficient C of an electron configuration obtained through a solution that will be described later. $h_{ab}$ and $(ab|cd)$ are a 1-electron integration and a 2-electron integration at a molecular-orbital base and are obtained through $h_{rs}$ and $(rs|tu)$ at an atomic orbital base. The $h_{rs}$ and $(rs|tu)$ are defined as below.

$$h_{rs} = \int_{-\infty}^{\infty} \int_{-\infty}^{\infty} \int_{-\infty}^{\infty} x_r(r_1) h x_s(r_1) dr_1, \qquad (3)$$

$$h = -\frac{\hbar}{2}\nabla^2 - \sum_{i=1}^{Nuc.} \frac{Z_i}{|r_1 - R_i|} \text{ (where } (\hbar = h/2\pi))$$

$$(rs|tu) = \qquad (4)$$
$$\int_{-\infty}^{\infty}\int_{-\infty}^{\infty}\int_{-\infty}^{\infty}\int_{-\infty}^{\infty}\int_{-\infty}^{\infty}\int_{-\infty}^{\infty} x_r(r_1) x_s(r_1) \frac{1}{|r_1-r_2|} x_t(r_2) x_u(r_2) dr_1 dr_2$$

Here, h indicates Planck's constant. Further, Nuc. stands for Nuclei and indicates the number of atoms. $Z_i$ indicates the electrical charges of the nuclei and $R_i$ indicates the positions of the nuclei. The relationship between s molecular orbital $\phi_a$ and an atomic orbital $\chi_x$ is shown as below.

$$\Phi_a = \sum_{r}^{N} C_{ra} X_r \qquad (5)$$

The integrations of the Equations (3) and (4) are transformed from the atomic orbital base to the molecular orbital base according to the relationship, as shown below.

$$h_{ab} = \sum_{r}^{N} \sum_{s}^{N} c_{ra} c_{sb} h_{rs} \qquad (6)$$

$$(ab|cd) = \sum_{r}^{N} \sum_{s}^{N} \sum_{t}^{N} \sum_{u}^{N} c_{ra} c_{sb} c_{tc} c_{ud} (rs|tu) \qquad (7)$$

Here, N indicates the number of atomic orbitals. Although the present invention is provided under the assumption that the number of the atomic orbitals is one thousand or more, this method can be used for a case where the number is less than that. $c_a$ is a transformation matrix shown in Equation (5) for transforming the atomic orbital into the molecular orbital and referred to as a molecular-orbital coefficient. $c_{sb}$ is another molecular-orbital coefficient. According to the MCSCF method, both the electron-configuration coefficient C and the molecular-orbital coefficient c are obtained by the variational method. However, the CI method is different from the above-described method in that only the coefficient C is obtained.

The electron-configuration coefficient C is obtained through the following equations.

$$\sum_{J}^{CSF}(H_{IJ} - \delta_{IJ}E)C_J = 0 \qquad (8)$$

$$H_{IJ} = \sum_{ab}^{MO} \gamma_{ab}^{IJ} h_{ab} + \frac{1}{2}\sum_{abcd}^{MO} \Gamma_{abcd}^{IJ}(ab|cd) \qquad (9)$$

Here, CSF is a configuration state function. A wave function is given as the linear combination of this asymmetric determinant CSF. $\delta_{IJ}$ is Kronecker delta. Where an expression I=J stands, the value of $\delta_{IJ}$ is one. At all other times, the value thereof is zero.

A predetermined amount is required for determining the molecular-orbital coefficient, as shown below.

$$y_{ac} = \sum_{b}\sum_{d}\sum_{x}\sum_{y}\{(ab|xy)\Gamma_{cdxy} + 2(ax|by)\Gamma_{cxdy}\}u_{bd} \qquad (10)$$

Here, $U_{bd}$ is a matrix relating to linear transformation of the molecular orbital.

In either the MCSCF method or the CI method, generation of a 2-electron integration (ab|cd) at the molecular-orbital base constitutes most part of the computing cost. According to the complete active space SCF (CASSCF) method, which is a typical method of the MCSCF method, electron excitation is allowed only within a predetermined molecular-orbital range, so as to simplify the formula. Where the number of molecular orbitals in the active space is determined to be n and the number of atomic-orbital bases therein is determined to be N, usually, the relationship between n and N is shown as n<<N. According to a known computing scheme, all the 2-electron integrations at the atomic-orbital bases are stored in a main memory or an external storage medium such as a disk, and transformation shown in Equation (7) is performed. The transformation algorithm is shown in FIGS. 5 and 6. In the case of a simple eight-deep DO loop including indexes a, b, c, and d of the molecular orbital and indexes r, s, t, and u of the atomic orbital, $n^4N^4$ multiplication is required. However, according to the above-described algorithm, the same result as that of the eight-deep DO loop can be obtained by executing a five-deep DO loop four times, and the operand is shown as $nN^4+n^2N^3+n^3N^2+n^4N$. For example, where n=10 and N=1000, the computing speed increases by about one thousand times. However, according to this method, many computer resources are required for storing the 2-electron integrations at the atomic-orbital bases and intermediate data midway through transformation. Therefore, this method is not suitable for calculating large-sized molecules.

In recent years, computers have achieved high-speed operation by using parallel processors. Therefore, according to either the MCSCF method or the CI method, the size of a molecule to be calculated by parallel processing needs to be increased and the computing cost needs to be decreased. The advantages of a parallel computer are shown below.

1. A high-speed operation computer can be achieved at low cost by connecting many commodity processors.

2. Through the use of many local memories of the processors, the computer obtains a large main-memory area, as a whole.

The 2-electron integration at the atomic-orbital base and that at the molecular-orbital base are independent of each other. Therefore, where these integrations are parallelized based on this characteristic, the following problems arise. That is to say, since all the 2-electron integrations at $N^4$ atomic-orbital bases are required for calculating one 2-electron integration at the molecular-orbital base, 1. distribution processing for distributing part of the 2-electron integrations at the atomic-orbital bases to the processors is performed, whereby all the $N^4$ 2-electron integrations have to be collected by each of the processors, which generates intercommunications between all the processors and become a bottleneck in communications, even though the integration-computing time can be reduced by parallelization.

2. Since all the integrations at the $N^4$ atomic-orbital bases need to be calculated in each of the processors for reducing the bottleneck in communications, the reduction of computing time through the parallelization cannot be achieved.

Thus, the above-described problems are mutually contradictory to each other.

Further, the computing performed according to Equation (2) and the integration of the molecular-orbital base are required for obtaining the derivative of a 2-electron integration with respect to a nuclear coordinate. In this case, problems same as the above-described problems occur.

DISCLOSURE OF INVENTION

The object of the present invention is to provide a parallel computing method for solving the above-described problems by using a parallel computer having a plurality of processors.

The parallel computing method according to the present invention will now be described as below.

(1) A parallel computing method by using a parallel computer having a plurality of processors, wherein when a 2-electron integration is transformed from an atomic-orbital base (rs|tu) to a molecular-orbital base (ab|cd), indexes r and s of an atomic orbital to be calculated are designated for the plurality of processors and each of the plurality of processors performs processing for all combinations of designated indexes R and S, and indexes t and u of the atomic orbital to be calculated.

(2) A parallel computing method by using a parallel computer having a plurality of processors, wherein when a 2-electron integration is transformed from an atomic-orbital base (rs|tu) to a molecular-orbital base (ab|cd), indexes r and s of an atomic orbital to be calculated are designated for the plurality of processors and each of the plurality of processors performs processing for all combinations of designated indexes r and s, and indexes t and u of the atomic orbital to be calculated, whereby data to be processed is divided so that grain sizes indicating the workload for the plurality of processors are equalized.

(3) In a parallel computing method according to the processing (1) or the processing (2), data transfer is not performed between the plurality of processors during the 2-electron integration computing and gathering is performed only once after the processing performed by the plurality of processors, so as to obtain the sum of data processed by the plurality of processors.

(4) In a parallel computing method according to the processing (1) or the processing (2), each of the plurality of processors 1) calculates a 2-electron integration (RS|tu) at an atomic-orbital base for all combinations of R and S designated for each of the processors, and t and u, 2) performs transformation from u to d for the calculated 2-electron integration, 3) performs transformation from t to c for the data transformed through the processing 2), 4) performs transformation from S to B that is a component of b for the data transformed through the processing 3), 5) performs transformation from R to A that is a component of a for the data transformed through the processing 4), 6) stores the data transformed through the processing 5) in a local memory of each of the processors, and 7) finally performs gathering, thereby obtaining the 2-electron integration (ab|cd) at the molecular-orbital base.

(5) In a parallel computing method according to the processing (1) or the processing (2), each of the plurality of processors 1) calculates a 2-electron integration (RS|tu) at an atomic-orbital base for all combinations of R and S designated for each of the processors, and t and u, 2) performs transformation from u to d for the calculated 2-electron integration, 3) performs transformation from t to c for the data transformed through the processing 2), 4) performs transformation from S to B that is a component of b for the data transformed through the processing 3), 5) does not transform R but stores in a local memory of each of the plurality of processors, as $V_{cbd(RS)}$, and 6) calculates the product sum of a transformation coefficient from R to a, a transformation coefficient between molecular orbitals, and the $V_{cbd(RS)}$, and stores the computing result in a local memory of each of the plurality of processors in repetition computings for $Y_{ac}$ indicating an amount required for determining a molecular-orbital coefficient.

(6) A parallel computing method by using a parallel computer having a plurality of processors, wherein a secondary density matrix Γ at a molecular-orbital base is transferred to each of the plurality of processors and inversely transformed from the molecular-orbital base to an atomic-orbital base in each of the plurality of processors, whereby indexes r and s of an atomic orbital to be calculated are designated for the plurality of processors, processing is performed for all combinations of the designated indexes R and S, and indexes t and u of the atomic orbital to be calculated, and data to be processed is divided so that grain sizes indicating a workload for the plurality of processors are equalized, where a derivative of a 2-electron integration with respect to an atomic-nuclear coordinate is calculated.

BRIEF DESCRIPTION OF THE DRAWINGS

FIG. 1 illustrates the first-half of distribution processing performed between processors, where the distribution processing is performed for 2-electron-integration transformation according to the present invention.

FIG. 4 illustrates a parallel algorithm obtained through inverse transformation of a secondary density matrix $\Gamma$ from the molecular-orbital base to the atomic-orbital base according to the present invention.

FIG. 5 illustrates steps 1 to 3 of $4N^5$ transformation algorithm used for transforming a 2-electron integration from an atomic-orbital base to a molecular-orbital base.

FIG. 6 illustrates step 4 of the $4N^5$ transformation algorithm used for transforming the 2-electron integration from the atomic-orbital base to the molecular-orbital base.

BEST MODE FOR CARRYING OUT THE INVENTION

Figure 2:
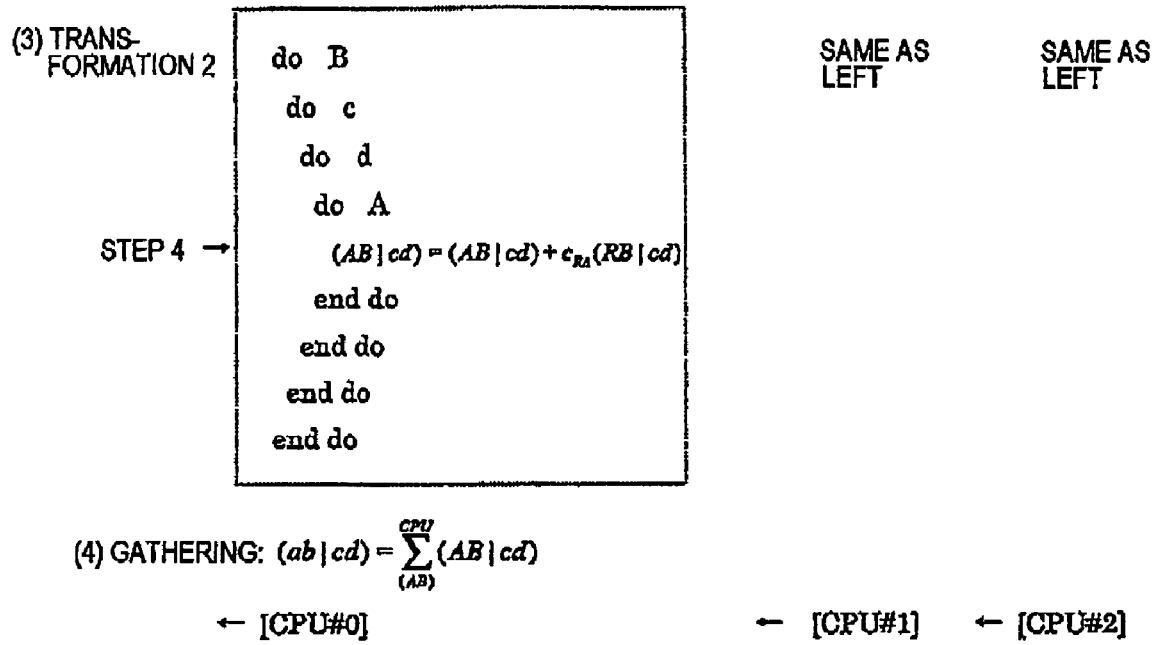
FIG. 2 illustrates the latter-half of the distribution processing performed between the processors, where the distribution processing is performed for the 2-electron-integration transformation according to the present invention.

Modes of the present invention will now be described.

According to the inventors of the present invention, since a 2-electron integration at an atomic-orbital base and a derivative with respect to an atomic-nuclear coordinate are independent of each other, parallelization by using indexes r and s of an atomic orbital is required for transformation from the atomic-orbital base to a molecular-orbital base. (That is to say, the indexes r and s of an atomic orbital to be calculated are designated for the plurality of processors and all the combinations of the designated indexes r and s, and indexes t and u are calculated in each of the processors, so that data to be processed is divided for obtaining equalized grain sizes. Parallelization is performed by the indexes r and s, and computing for all the combinations of these indexes and the indexes t and u is performed in each of the processors. Therefore, floating-point arithmetic needs to be performed on an average of ten thousand times for one 2-electron integration. Subsequently, each of the processors has to perform $10000N^2$ computings, whereby sufficiently large grain sizes can be obtained. The grain sizes need to be equalized and maximized, and the number of transfer between the processors needs to be decreased for increasing parallel-computing performance. This configuration will be illustrated later. According to computing procedures of the present invention, data transfer is not performed between the processors during the 2-electron-integration computing and gathering is performed once after the transformation.

According to a solution for obtaining a coefficient C of electron configuration, parallelization is performed by the indexes r and s of the atomic orbital. The computing procedures in each of the processors are described below.

1) A 2-electron integration (RS|tu) at the atomic-orbital base is calculated for all the combinations of R and S designated for each processor, and t and u.

2) Transformation from u to d is performed for the calculated 2-electron integration.

3) Transformation from t to c is performed.

4) Transformation from S to B is performed.

5) Transformation from R to A is performed.

The transformation data is stored in a local memory of each of the processors. Finally, gathering is performed for obtaining a 2-electron integration (ab|cd) at the molecular-orbital base.

According to a repetition solution for obtaining a coefficient c of the molecular orbital, parallelization is performed by the indexes r and s of the atomic orbital. The computing procedures performed in each of the processors are described below.

1) A 2-electron integration (RS|tu) at the atomic-orbital base is calculated for all the combinations of R and S designated for each processor, and t and u.

2) Transformation from u to d is performed for the calculated 2-electron integration.

3) Transformation from t to c is performed.

4) Transformation from S to B is performed.

5) R is not transformed but stored in the local memory, as $V_{cbd(RS)}$.

6) The product sum of a transformation coefficient ($C_{Ra}$) from R to a and a transformation coefficient ($u_{bd}$) between the molecular orbitals is calculated concurrent with repetition computing of $Y_{ac}$ (see Equation (13). Since the local memory of each processor stores $V_{cbd(RS)}$ having a little amount of data, a work area on the main memory is prevented from being increased due to the repetition computing.

In the energy-gradient computing, the secondary-density matrix $\Gamma$ at the molecular-orbital base is transferred to each of the processors and inverse transformation from the molecular-orbital base to the atomic-orbital base is performed. Subsequently, parallelization is performed by the indexes r and s of the atomic orbital, whereby the configuration becomes the same as in the case of the 2-electron-integration computing. In this case, the derivative of only an atomic orbital r with respect to a nuclear coordinate needs to be obtained.

Embodiments of the present invention will now be described.

According to solutions for obtaining the electron-configuration coefficient C and the molecular-orbital coefficient c according to the MCSCF method and the electron-configuration coefficient C in the CI method, a repetition solution is widely used for reducing the work area on a main memory. Therefore, intermediate data such as the 2-electron integration at the molecular-orbital base needs to be stored. The parallel computer can store the intermediate data due to the above-described advantage given under 2. (Through the use of many local memories of the processors, the computer obtains a large main memory area, as a whole.). On the other hand, since the repetition computing is unnecessary for the energy-gradient computing, the present invention achieves a parallel algorithm based on basic ideas given under 1) and 2).

1) For determining the electron-configuration coefficient C and the molecular-orbital coefficient c, where the relationship between n and N is shown as n<<N, intermediate data such as the 2-electron integration at the molecular-orbital base, where the amount of the 2-electron integration is little, is stored on the main memory on each of the processors and used repetitively.

2) In the energy-gradient computing, γ and Γ of the molecular-orbital base are inversely transformed to the atomic-orbital base and subjected to parallel computing based on an equation for the atomic-orbital base, as shown below.

$$\frac{\partial E}{\partial q} = \sum_{rs}^{AO} \gamma_{rs} \frac{\partial h_{rs}}{\partial q} + \sum_{rstu}^{AO} \Gamma_{rstu} \frac{\partial (rs|tu)}{\partial q} - \sum_{rs}^{AO} W_{rs} \frac{\partial S_{rs}}{\partial q} \quad (11)$$

Here, AO stands for an atomic orbital. W indicates an amount used for the energy-gradient method. This amount is obtained by calculating the product of orbital energy and the molecular-orbital coefficient. Further, $S_{rs}$ indicates an overlap integration.

First, a method for generating a 2-electron integration at a molecular-orbital base is described, where the molecular-orbital base belongs to an active space required for determining the electron-configuration coefficient C. Parallelization is performed by the indexes r and s of the atomic orbital. Further, a 2-electron integration (RS|tu) at the atomic-orbital base is calculated for all t and u in each of the processors. The basic algorithm is shown in FIGS. 1 and 2. Here, R and S of the indexes of the atomic orbital, where the indexes are designated as r and s, indicate an atomic orbital allocated to a predetermined processor. An equation is provided as below.

$$(ab|cd) = \sum_A \sum_B (c_{RA} R c_{SB} S | cd) = \sum_A \sum_B (AB|cd) \quad (12)$$

Here, according to the relationship shown in Equation (5), A and B include only R and S designated for each processor, where the R and S is included in linear-combination components of atomic orbitals r and s with reference to molecular orbitals a and b. Finally, (AB|cd) is gathered, whereby correct (ab|cd) is obtained. According to this relationship, the computing procedures performed in each of the processors are provided as below.

1) A 2-electron integration (RS|tu) at the atomic-orbital base is calculated for all the combinations of R and S designated for each processor, and t and u.
2) Transformation from u to d is performed for the calculated 2-electron integration.
3) Transformation from t to c is performed.
4) Transformation from S to B is performed.
5) Transformation from R to A is performed.

It should be noted that no communications between the processors are generated during the steps 1) to 5) are performed and that the number of the 2-electron integrations at the atomic-orbital bases to be calculated in all the processors becomes $N^4$. Finally, (AB|cd) on each of the processors is gathered, so as to obtain (ab|cd). The transfer amount is $n^4$ at most. Since n is the order of 10 and the transfer is performed in one direction to a master processor, the transfer time presents no problem. Further, where the number of the processors is small, R and S may be grouped, as required, for achieving parallelization in a like manner. The number of entire computings according to known methods is $nN^4+n^2N^3+n^3N^2+n^4N$, as described above. According to this method, however, since computings at steps 1 to 4 are performed in $N^2$ processors, the number of entire computings is $N^2(nN^2+n^2N+n^3+n^4)+n^4N^2$. Thus, the number of computings according to this method increases by $n^4N(N-1)+n^4N^2$ through parallelization.

Next, parallelization of Equation (10) necessary for determining the molecular-orbital coefficient c will be described. Part of Equation (10) is now shown as the atomic-orbital base.

$$y_{ac} = \sum_b \sum_d \sum_x \sum_y \{(ab|xy)\Gamma_{cxdy} + 2(ax|by)\Gamma_{cxdy}\}u_{bd} \quad (13)$$

$$= \sum_b \sum_d \sum_x \sum_y \left\{ \sum_R \sum_S (c_{Ra} R c_{Sb} S | xy)\Gamma_{cdxy} + 2 \sum_R \sum_S (c_{Ra} R c_{Sx} S | by)\Gamma_{cxdy} \right\} u_{bd}$$

$$= \sum_R \sum_S \sum_b \sum_d \sum_x \sum_y \{(c_{Ra} R c_{Sb} S | xy)\Gamma_{cdxy} + 2(c_{Ra} R c_{Sx} S | by)\Gamma_{cxdy}\} u_{bd}$$

$$= \sum_R \sum_S c_{Ra} \sum_b \sum_d \sum_x \sum_y \{(R c_{Sb} S | xy)\Gamma_{cdxy} + 2(R c_{Sx} S | by)\Gamma_{cxdy}\} u_{bd}$$

$$= \sum_R \sum_S c_{Ra} \sum_b \sum_d V_{cbd(RS)} u_{bd}$$

$$= \sum_R \sum_S Y_{ac(RS)}$$

Figure 3:
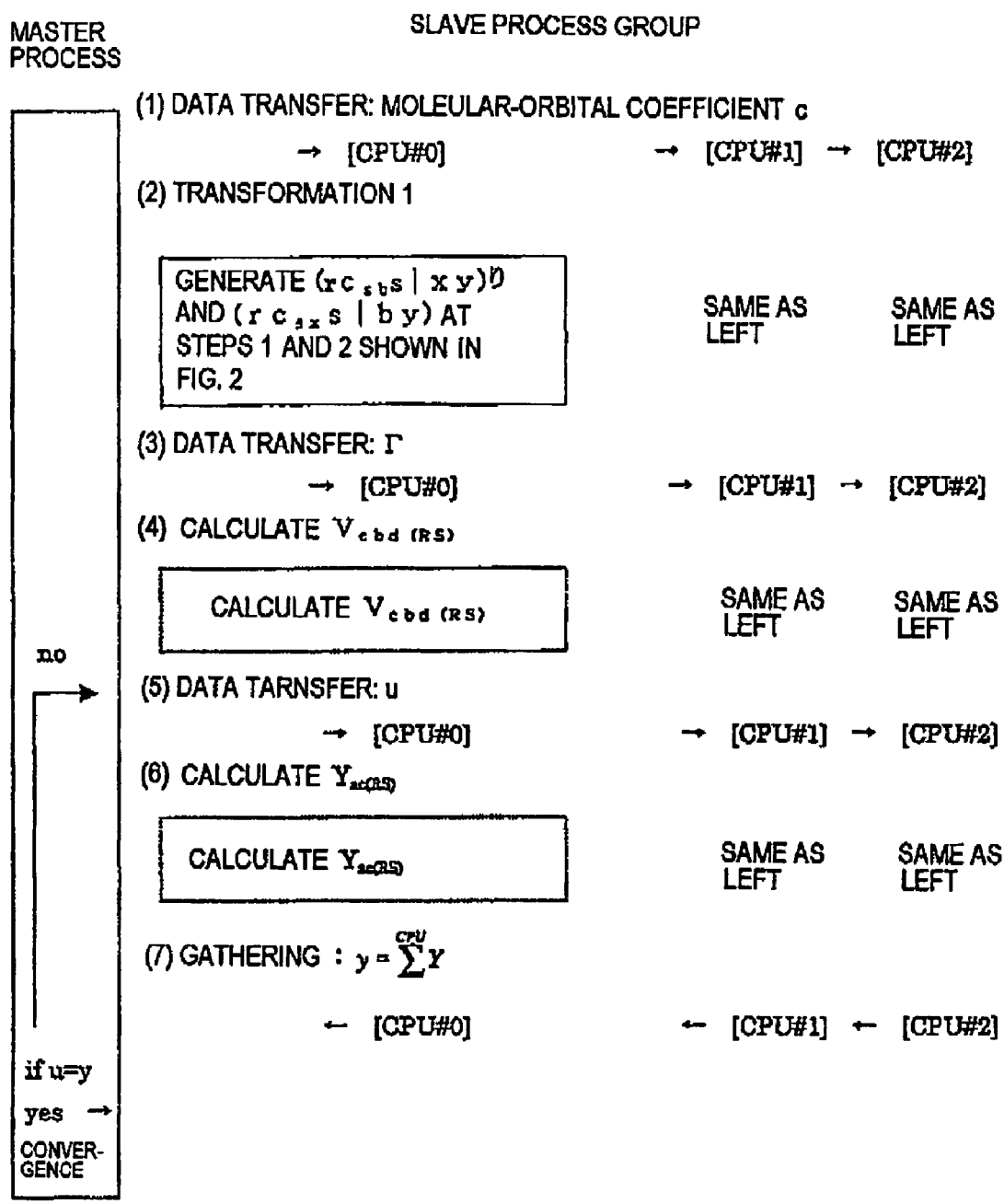
FIG. 3 illustrates distribution processing performed between the processors, where the distribution processing is performed for molecular-orbital-coefficient determination repetition computing according to the present invention.

Further, according to Equation (12), $Y_{ac(RS)}$ can also be gathered, where it is determined to be a part calculated in each of the processors (CPU: Central Processing Unit). It should be noted that the value of transfer-data amount is $N^2$. Subsequently, $y_{ac}$ can be obtained through performing parallelization by r and s and gathering $Y_{ac(RS)}$ calculated in each of the processors. The data flow is shown in FIG. 3. The reason why data is stored, as $V_{cbd(RS)}$, in each of the processors is shown below. Since a and b in Equation (10) become all the molecular orbitals in principle, the dimension number thereof is N, where the dimension number of x and y is n. Subsequently, the size of the first and second terms becomes $n^2N^2$. Since r is stored without being transformed, the number of computings increases. However, the size of the work area is reduced to $n^2N$. Further, where (ab|xy) is gathered, the data amount becomes $n^2N^2$. However, the amount is cut to $N^2$ by calculating the sum of x and y in each of the processors before the transfer, whereby the transfer data amount reduces.

Finally, parallelization of 2-electron integrations by an atomic-nuclear coordinate will now be described. This parallelization is performed for the energy-gradient computing. As described above, this computing method does not require repetition computings. Therefore, the parallelization is achieved by transferring Γ whose data amount is as small as $n^4$ to each of the processors and inversely transforming it from the molecular-orbital base to the atomic-orbital base. This inverse-transformation algorithm is shown in FIG. 4. The parallelization is performed by using r and s and computings are performed for all t and u, as in the case of an ordinary 2-electron integration, except that the depth number of the DO loop is seven. The second term of Equation (11) calculated by each of the processors is added to an array keeping a force applied to an atomic nucleus on the processor, and gathered. The size of the array is 3× the atom number and does not become a bottleneck in transfer.

The number of computings for the inverse transformation of Γ is the same as that of the known methods.

According to the above-described parallel algorithm, the parallelization is performed by the indexes r and s of the atomic orbital. Therefore, the grain sizes are equalized, as the number of processors increases, whereby high scalability is maintained. Further, since the suitable number of processors is $N^2$, this method can be used for one million parallel computers, where N=1000.

The following Tables 1 and 2 illustrate the known computing method, the computing number of this method, and expressions of computings performed in the work area. Although the computing number increases a little due to the parallelization, the size of the work area in each of the processors decreases by a factor of $N^2$. Subsequently, this algorithm can effectively use inexpensive local memories.

TABLE 1

Comparison between computing amount and work area for 2-electron integration transformation according to known transformation method, and those according to transformation method of the present invention

| | $N^5$ multiplication method | | This method (Note 1) | |
|---|---|---|---|---|
| | Computing Amount | Work Area | Computing Amount | Work Area |
| STEP 1 | $N^4 n$ | $N^4 + N^3 n$ | $N^2 n$ | $N^2 + Nn$ |
| STEP 2 | $N^3 n^2$ | $N^3 n + N^2 n^2$ | $Nn^2$ | $Nn + n^2$ |
| STEP 3 | $N^2 n^3$ | $N^2 n^2 + Nn^3$ | $n^3$ | $n^2 + n^3$ |
| STEP 4 | $Nn^4$ | $Nn^3 + n^4$ | $n^4$ | $n^3 + n^4$ |
| Gathering | — | — | $N^2 n^4$ | |

Note 1)
where $N^2$ processors are used

TABLE 2

Comparison between computing amount and work area for molecular-orbital coefficient determination according to known transformation method, and those according to transformation method of the present invention

| | $N^5$ multiplication method | | This method (Note 1) | |
|---|---|---|---|---|
| | Computing Amount | Work Area | Computing Amount | Work Area |
| STEP 1 | $N^4 n$ | $N^4 + N^3 n$ | $N^2 n$ | $N^2 + Nn$ |
| STEP 2 | $N^3 n^2$ | $N^3 n + N^2 n^2$ | $Nn^2$ | $Nn + n^2$ |
| STEP 3 | $N^3 n^2$ | $2(N^2 n^2)$ | $Nn^2$ | $n^2 + Nn^2$ |
| STEP 4 | $N^3 n^2$ | $2(N^2 n^2)$ | $N^2 n^2$ | $Nn^2 + Nn^3$ |
| Gathering | — | — | $N^2$ | |

Note 1)
where $N^2$ processors are used

As has been described, the present invention provides a parallel computing method using a parallel computer having a plurality of processors. According to this method, where a 2-electron integration is transformed from an atomic-orbital base (rs|tu) to a molecular-orbital base (ab|cd), indexes r and s of an atomic orbital to be calculated are designated for the plurality of processors. Further, each of the plurality of processors performs processing for all the combinations of designated indexes R and S, and indexes t and u of the atomic orbital to be calculated. Therefore, equalized grain sizes are obtained and many commodity processors can be connected to the parallel computer, with high performance. Therefore, the cost of the high-speed operation computer reduces. Further, since the computer can use inexpensive local memories, it can secure a large main-memory area, as a whole.

The invention claimed is:

1. A parallel computing method for transforming a 2-electron integration from an atomic-orbital base (rs|tu) to a molecular-orbital base (ab|cd) using a parallel computer having a plurality of processors, the method reducing an amount of computations by calculating at least three of the four indexes among (ab|cd) at the molecular orbital base, the method comprising:

designating indexes r and s for the plurality of processors to calculate 2-electron integration (RS|tu) at the atomic orbital base, wherein designated indexes R and S indicate an atomic orbital allocated to a predetermined processor from the plurality of processors;

performing processing for all combinations of designated indexes R and S and indexes t and u of the atomic orbital in parallel by the plurality of processors to calculate the at least three of the four indexes among (ab|cd) at the molecular orbital base; and storing the at least three of the four calculated indexes among (ab|cd) at the molecular orbital base in a memory.

2. The parallel computing method according to claim 1, wherein data transfer is not performed between the plurality of processors during the 2-electron integration computing and wherein gathering is performed only once after the processing performed by the plurality of processors, so as to obtain the sum of data processed by the plurality of processors.

3. The parallel computing method according to claim 1, wherein each of the plurality of processors (1) calculates the 2-electron integration (RS|tu) at the atomic-orbital base for all combinations of R and S designated for each of the processors, and t and u, (2) performs transformation from u to d for the calculated 2-electron integration, (3) performs transformation from t to c for the data transformed through the processing (2), (4) performs transformation from S to B that is a component of b for the data transformed through the processing (3), (5) performs transformation from R to A that is a component of a for the data transformed through the processing (4), (6) stores the data transformed through the processing (5) in a local memory of each of the processors, and (7) finally performs gathering, thereby obtaining the 2-electron integration (ab|cd) at the molecular-orbital base.

4. The parallel computing method according to claim 1, wherein each of the plurality of processors (1) calculates the 2-electron integration (RS|tu) at the atomic-orbital base for all the combinations of R and S designated for each of the processors, and t and u, (2) performs transformation from u to d for the calculated 2-electron integration, (3) performs transformation from t to c for the data transformed through the processing (2), (4) performs transformation from S to B that is a component of b for the data transformed through the processing (3), (5) does not transform R but stores in a local memory of each of the plurality of processors, as $V_{cbd(RS)}$, and (6) calculates the product sum of a transformation coefficient from R to a, a transformation coefficient between molecular orbitals, and the $V_{cbd(RS)}$, and stores the computing result that is the calculated product sum in a local memory of each of the plurality of processors in repetition computings for $Y_{ac}$ indicating an amount required for determining a molecular-orbital coefficient.

5. The parallel computing method according to claim 3, wherein designated indexes R and S are included in linear combination components of atomic-orbitals r and s with reference to molecular-orbitals a and b.

6. A parallel computing method for transforming a 2-electron integration from an atomic-orbital base (rs|tu) to a molecular-orbital base (ab|cd) using a parallel computer having a plurality of processors, the method reducing an amount of computations by calculating at least three of the four indexes among (ab|cd) at the molecular orbital base, the method comprising:

dividing data to be processed so that grain sizes indicating the workload for the plurality of processors are equalized;

designating indexes r and s for the plurality of processors to calculate 2-electron integration (RS|tu) at the atomic orbital base, wherein designated indexes R and S indicate an atomic orbital allocated to a predetermined processor from the plurality of processors;

performing processing for all combinations of the designated indexes R and S and indexes t and u of the atomic orbital in parallel by the plurality of processors to calculate the at least three of the four indexes among (ab|cd) at the molecular orbital base; and storing the at least three of the four calculated indexes among (ab|cd) at the molecular orbital base in a memory.

7. The parallel computing method according to claim 6, wherein data transfer is not performed between the plurality of processors during the 2-electron integration computing and wherein gathering is performed only once after the processing performed by the plurality of processors, so as to obtain the sum of data processed by the plurality of processors.

8. The parallel computing method according to claim 6, wherein each of the plurality of processors (1) calculates the 2-electron integration (RS|tu) at the atomic-orbital base for all the combinations of R and S designated for each of the processors, and t and u, (2) performs transformation from u to d for the calculated 2-electron integration, (3) performs transformation from t to c for the data transformed through the processing (2), (4) performs transformation from S to B that is a component of b for the data transformed through the processing (3), (5) performs transformation from R to A that is a component of a for the data transformed through the processing (4), (6) stores the data transformed through the processing (5) in a local memory of each of the processors, and (7) finally performs gathering, thereby obtaining the 2-electron integration (ab|cd) at the molecular-orbital base.

9. The parallel computing method according to claim 6, wherein each of the plurality of processors (1) calculates the 2-electron integration (RS|tu) at the atomic-orbital base for all combinations of R and S designated for each of the processors, and t and u, (2) performs transformation from u to d for the calculated 2-electron integration, (3) performs transformation from t to c for the data transformed through the processing (2), (4) performs transformation from S to B that is a component of b for the data transformed through the processing (3), (5) does not transform R but stores in a local memory of each of the plurality of processors, as Vcbd(RS), and (6) calculates the product sum of a transformation coefficient from R to a, a transformation coefficient between molecular orbitals, and the Vcbd(RS), and stores the computing result that is the calculated product sum in a local memory of each of the plurality of processors in repetition computings for $Y_{ac}$ indicating an amount required for determining a molecular-orbital coefficient.

10. The parallel computing method according to claim 8, wherein designated indexes R and S are included in linear combination components of atomic-orbitals r and s with reference to molecular-orbitals a and b.

11. A parallel computing method using a parallel computer having a plurality of processors, wherein a secondary density matrix Γ (abcd) at a molecular-orbital base is inversely transformed from the molecular-orbital base to an atomic-orbital base, the atomic orbital base having four indexes (RStu), and calculating a derivative of a 2-electron integration at the atomic orbital base with respect to an atomic-nuclear coordinate, the method reducing an amount of computations by calculating all the four indexes (RStu) at the atomic orbital base in parallel, the method comprising:

dividing data to be processed so that grain sizes indicating a workload for the plurality of processors are equalized;

transferring the secondary density matrix Γ to each of the plurality of processors;

performing parallel processing to compute the inverse transformation of the secondary density matrix Γ (abcd) from the molecular-orbital base to the atomic-orbital base to obtain secondary density matrix Γ (RStu) at the atomic orbital base, wherein all the four indexes (RStu) at the atomic orbital base are calculated in parallel by the each of the plurality of processors;

designating indexes R and S of the atomic orbital indexes computed above for the plurality of processors to calculate a 2-electron integration (RS|tu) at the atomic orbital base, performing processing for all combinations of the designated indexes R and S and indexes t and u of the atomic orbital to calculate the 2-electron integration (RS|tu) at the atomic orbital base;

calculating the derivative of the 2-electron integration (RS|tu) with respect to the atomic-nuclear coordinate; and storing said calculated derivative of the 2-electron integration (RS|tu) with respect to the atomic nuclear coordinate in a memory.

* * * * *